United States Patent
Kang et al.

(10) Patent No.: US 10,517,572 B2
(45) Date of Patent: Dec. 31, 2019

(54) ULTRASOUND IMAGING APPARATUS AND METHOD OF CONTROLLING ULTRASOUND IMAGING APPARATUS

(71) Applicant: SAMSUNG MEDISON CO., LTD., Hongcheon-gun, Gangwon-do (KR)

(72) Inventors: Dae-woong Kang, Gangwon-do (KR); Kyung-dong Kim, Gangwon-do (KR)

(73) Assignee: Samsung Medison Co., Ltd., Hongcheon-gun, Gangwon-do (KR)

( * ) Notice: Subject to any disclaimer, the term of this patent is extended or adjusted under 35 U.S.C. 154(b) by 226 days.

(21) Appl. No.: 14/634,690

(22) Filed: Feb. 27, 2015

(65) Prior Publication Data

US 2015/0245821 A1    Sep. 3, 2015

(30) Foreign Application Priority Data

Feb. 28, 2014   (KR) ........................ 10-2014-0023796

(51) Int. Cl.
  *A61B 8/00*   (2006.01)
  *G06T 7/00*   (2017.01)
  *A61B 8/08*   (2006.01)

(52) U.S. Cl.
  CPC .............. *A61B 8/54* (2013.01); *A61B 8/4245* (2013.01); *A61B 8/4455* (2013.01); *A61B 8/461* (2013.01); *A61B 8/5207* (2013.01); *A61B 8/565* (2013.01); *G06T 7/0012* (2013.01)

(58) Field of Classification Search
  CPC ..... A61B 8/4245; A61B 8/4455; A61B 8/461; A61B 8/5207; A61B 8/54; A61B 8/565; G06T 7/0012
  See application file for complete search history.

(56) References Cited

U.S. PATENT DOCUMENTS

| | | | |
|---|---|---|---|
| 9,186,127 B2* | 11/2015 | Kurt | ................. A61B 8/467 |
| 9,232,932 B2* | 1/2016 | Kim | ................. G01S 15/8984 |
| 9,986,977 B2* | 6/2018 | Kim | ................. A61B 8/54 |
| 2006/0173336 A1* | 8/2006 | Goubergen | ......... A61B 5/0456 600/450 |
| 2007/0083115 A1 | 4/2007 | Lee et al. | |
| 2007/0093713 A1 | 4/2007 | Byron | |
| 2008/0004608 A1 | 1/2008 | Dacquay et al. | |

(Continued)

FOREIGN PATENT DOCUMENTS

JP    2007-282957 A    11/2007
KR   10-2007-0017882 A   2/2007

(Continued)

OTHER PUBLICATIONS

Notice of Allowance issued in corresponding Korean Patent Application No. 10-2014-0023796, dated Jan. 18, 2016; with English translation.

(Continued)

*Primary Examiner* — Amanda Lauritzen Moher
(74) *Attorney, Agent, or Firm* — Morgan, Lewis & Bockius LLP

(57) ABSTRACT

Provided are an ultrasound imaging apparatus including a probe and a method of controlling the ultrasound imaging apparatus. The method includes: comparing a signal value acquired through an input unit with first and second threshold values; and performing an operation that is determined based on a result of the comparison.

13 Claims, 6 Drawing Sheets

(56) References Cited

U.S. PATENT DOCUMENTS

| | | | |
|---|---|---|---|
| 2009/0124903 A1* | 5/2009 | Osaka | A61B 8/12 |
| | | | 600/443 |
| 2009/0131793 A1 | 5/2009 | Stonefield et al. | |
| 2011/0141052 A1 | 6/2011 | Bernstein et al. | |
| 2011/0301465 A1* | 12/2011 | Waki | A61B 8/08 |
| | | | 600/445 |
| 2012/0053465 A1* | 3/2012 | Kudoh | A61B 8/4254 |
| | | | 600/443 |
| 2012/0197122 A1* | 8/2012 | Kurt | A61B 8/467 |
| | | | 600/440 |
| 2013/0137989 A1 | 5/2013 | Chen et al. | |
| 2013/0184582 A1* | 7/2013 | Kanayama | A61B 8/463 |
| | | | 600/440 |
| 2014/0163378 A1* | 6/2014 | Ohshima | A61B 8/4472 |
| | | | 600/447 |
| 2014/0316271 A1 | 10/2014 | Hyun | |
| 2015/0320388 A1 | 11/2015 | Ahn et al. | |

FOREIGN PATENT DOCUMENTS

| | | |
|---|---|---|
| KR | 10-0793295 B1 | 1/2008 |
| KR | 10-2012-0097324 A | 9/2012 |
| KR | 10-2013-0004854 A | 1/2013 |
| KR | 10-2013-0061103 A | 6/2013 |

OTHER PUBLICATIONS

Korean Notice of Non-Final Rejection issued in corresponding Korean Patent Application No. 10-2014-0023796, dated Jul. 13, 2015; with English translation.

* cited by examiner

ULTRASOUND IMAGING APPARATUS AND METHOD OF CONTROLLING ULTRASOUND IMAGING APPARATUS

RELATED APPLICATION

This application claims the benefit of Korean Patent Application No. 10-2014-0023796, filed on Feb. 28, 2014, in the Korean Intellectual Property Office, the disclosure of which is incorporated herein in its entirety by reference.

BACKGROUND

1. Field

One or more embodiments of the present invention relate to an ultrasound imaging apparatus and a method of controlling the ultrasound imaging apparatus, and more particularly, to an ultrasound imaging apparatus and a method of controlling the ultrasound imaging apparatus that allows a user to conveniently control the ultrasound imaging apparatus.

2. Description of the Related Art

Various types of medical imaging devices are used to identify the internal structures of a human body and diagnose diseases. Examples of medical imaging devices may include a magnetic resonance imaging (MRI) device, a computed tomography (CT) device, an ultrasound diagnosis device, a Positron Emission Tomography (PET) device, and an X-ray system.

Some medical imaging apparatuses may include a probe to acquire a medical image. For example, an ultrasound imaging apparatus transmits an ultrasound signal generated by a transducer in a probe to an object, receives information about an echo signal reflected from an object, and acquires an image of a portion inside the object. In particular, an ultrasound imaging apparatus is used for medical purposes such as observation of the internal structure of an object, detection of a foreign material, and measurement of injuries. An ultrasound imaging apparatus has high stability compared to X-ray diagnostic equipment, allows real-time display of an image, and is highly safe due to no exposure to radiation. Therefore, ultrasound imaging apparatuses have been widely used together with other types of imaging diagnosis devices.

SUMMARY

One or more embodiments of the present invention include an ultrasound imaging apparatus including a single input device through which a user is able to easily control the ultrasound imaging apparatus and a method of easily controlling the ultrasound imaging apparatus.

Additional aspects will be set forth in part in the description which follows and, in part, will be apparent from the description, or may be learned by practice of the presented embodiments.

According to one or more embodiments of the present invention, a method of controlling an ultrasound imaging apparatus includes: comparing a signal value acquired through an input unit with first and second threshold values; and performing an operation that is determined based on a result of the comparison, wherein the first threshold value is less than the second threshold value.

The input unit may be disposed on one side of a probe in the ultrasound imaging apparatus.

The comparing of the signal value acquired through the input unit with the first and second threshold values may include acquiring a signal that is determined according to the magnitude of a pressure applied to the input unit.

The comparing of the signal value acquired through the input unit with the first and second threshold values may include determining a state of the input unit based on the result of the comparison, and the performing of the operation that is determined based on the result of the comparison may include determining an operation corresponding to a change in the state of the input unit.

The change in the state of the input unit may include at least one of a transition of the state and a length of time during which the state of the input unit remains the same.

The performing of the operation that is determined based on the result of the comparison may include: displaying an ultrasound image acquired through the probe when the input unit is in a first state in which the signal value is less than or equal to the first threshold value; and stopping the ultrasound image being displayed when the input unit changes from the first state to a second state in which the signal value is greater than the first threshold value and less than or equal to the second threshold value.

The performing of the operation that is determined based on the result of the comparison may further include storing the displayed still image when the input unit changes from the second state to a third state in which the signal value is greater than the second threshold value.

The performing of the operation that is determined based on the result of the comparison may further include storing the displayed still image when a length of time during which the input unit remains in the second state is greater than or equal to a third threshold value.

The performing of the operation that is determined based on the result of the comparison may include: displaying an ultrasound image acquired through the probe when the input unit is in a first state in which the signal value is less than or equal to the first threshold value; and storing the ultrasound image as a moving image when the input unit changes from the first state to a third state in which the signal value is greater than the second threshold value.

The performing of the operation that is determined based on the result of the comparison may further include terminating the storing of the ultrasound image as the moving image when the input unit changes from the third state to the first state.

The performing of the operation that is determined based on the result of the comparison may further include displaying a still image when the input unit changes from the third state to a second state in which the signal value is greater than the first threshold value and is less than or equal to the second threshold value.

The comparing of the signal value acquired through the input unit with the first and second threshold values may include acquiring a signal that is determined according to a position of the input unit.

According to one or more embodiments of the present invention, an ultrasound imaging apparatus includes: an input unit for acquiring a signal value; a controller for determining a state of the input unit based on a result of comparing the signal value acquired through the input unit with first and second threshold values; and an image processing unit for performing image processing according to the state of the input unit determined by the controller, wherein the first threshold value is less than the second threshold value.

The input unit may be disposed on one side of a probe in the ultrasound imaging apparatus.

The input unit may acquire a signal that is determined according to the magnitude of a pressure applied to the input unit.

When the state of the input unit changes, the image processing unit may perform image processing according to the change in the state of the input unit.

The change in the state of the input unit may include at least one of a transition of the state and a length of time during which the state of the input unit remains the same.

The image processing unit may display an ultrasound image acquired through the probe through a display unit when the input unit is in a first state in which the signal value is less than or equal to the first threshold value, and stop the ultrasound image being displayed when the input unit changes from the first state to a second state in which the signal value is greater than the first threshold value and less than or equal to the second threshold value.

The image processing unit may store the displayed still image in a memory when the input unit changes from the second state to a third state in which the signal value is greater than, the second threshold value.

The image processing unit may store the displayed still image in a memory when a length of time during which the input unit remains in the second state is greater than or equal to a third threshold value.

The image processing unit may display an ultrasound image acquired through the probe through a display unit when the input unit is in a first state in which the signal value is less than or equal to the first threshold value, and store the ultrasound image as a moving image when the input unit changes from the first state to a third state in which the signal value is greater than the second threshold value.

The image processing unit may terminate the storing of the ultrasound image as the moving image when the input unit changes from the third state to the first state.

The image processing unit may display a still image when the input unit changes from the third state to a second state in which the signal value is greater than the first threshold value and is less than or equal to the second threshold value.

The input unit may acquire a signal that is determined according to a position of the input unit.

According to one or more embodiments of the present invention, a non-transitory computer-readable recording medium has recorded thereon a program for executing the above method on a computer.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
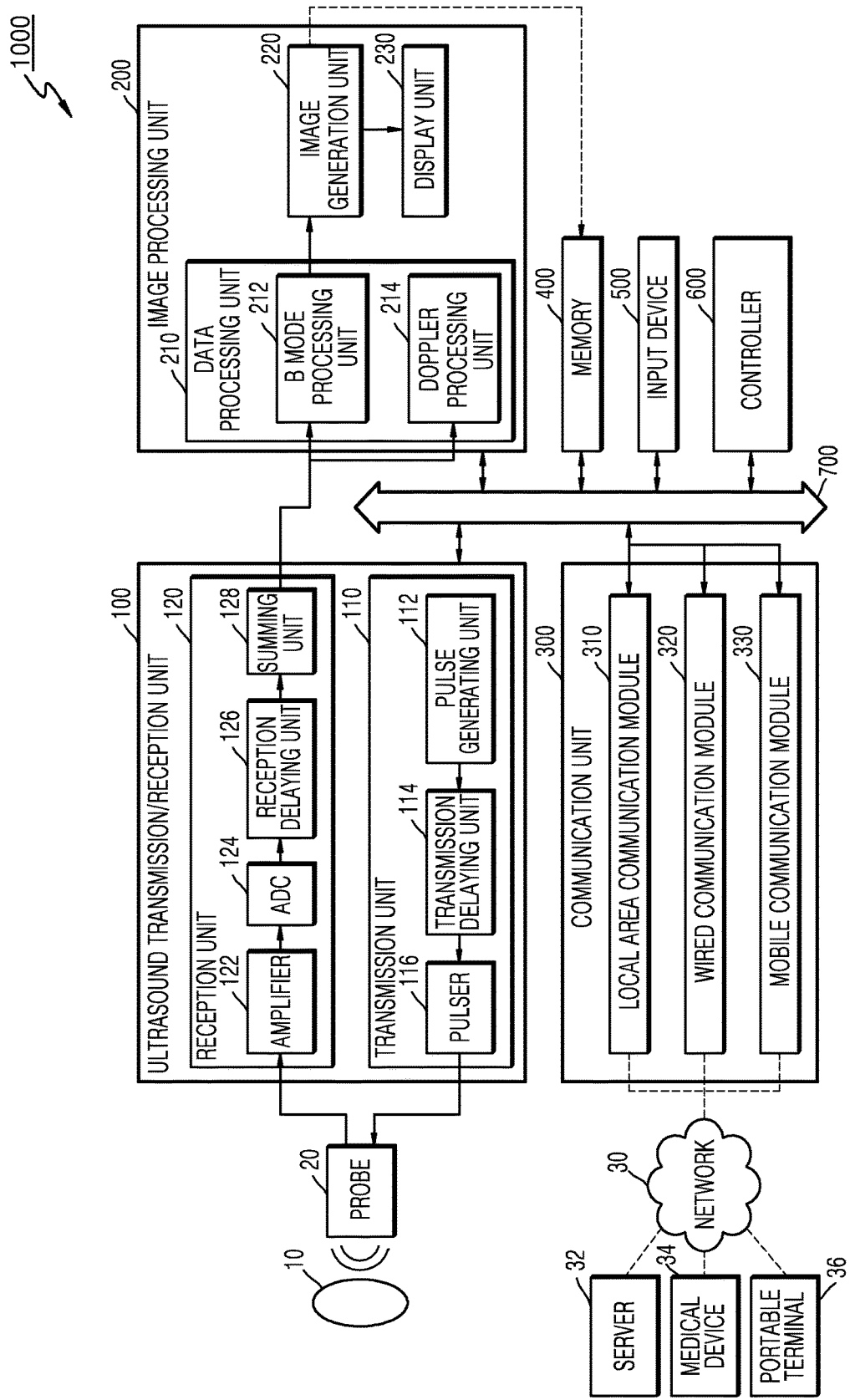
FIG. 1 is a block diagram of a configuration of an ultrasound diagnostic device related to an exemplary embodiment of the present invention.

Exemplary embodiments of the present invention will now be described more fully hereinafter with reference to the accompanying drawings so that they may be easily implemented by one of ordinary skill in the art. However, the present embodiments may have different forms and should not be construed as being limited to the descriptions set forth herein. In addition, parts not related to the present invention are omitted to clarify the description of exemplary embodiments of the present invention. In the accompanying drawings, like reference numerals refer to like elements throughout.

Throughout the specification, it will be understood that when an element is referred to as being "connected" or "coupled" to another element, it can be directly connected to or electrically coupled to the other element with one or more intervening elements interposed therebetween. Expressions such as "at least one of," when preceding a list of elements, modify the entire list of elements and do not modify the individual elements of the list.

Throughout the specification, it will also be understood that when a component "includes" an element, unless there is another opposite description thereto, it should be understood that the component does not exclude another element but may further include the element. In addition, terms such as " . . . unit", " . . . module", or the like refer to units that perform at least one function or operation, and the units may be implemented as hardware or software or as a combination of hardware and software. Expressions such as "at least one of," when preceding a list of elements, modify the entire list of elements and do not modify the individual elements of the list.

Throughout the specification, an "ultrasound image" refers to an image of an object obtained using an ultrasound wave. Furthermore, in the present specification, an "object" may include a person or an animal, or a part of a person or an animal. For example, the object may include organs such as the liver, the heart, the womb, the brain, a breast, and the abdomen, or a blood vessel. The "object" may also include a phantom. The phantom means a material having a volume that is approximately close to the density and effective atomic number of a living organism.

Furthermore, in the present specification, a "user" refers to a medical professional, such as a doctor, a nurse, a medical laboratory technologist, a medical imaging expert, and a technician who repairs a medical apparatus, but the user is not limited thereto.

Furthermore, throughout the specification, a controller and an image processing unit are described as separate components. However, the controller and the image processing unit may be realized by a single hardware or software module.

Embodiments of the present invention will now be described more fully with reference to the accompanying drawings, in which illustrative embodiments of the invention are shown.

In one embodiment, a medical imaging apparatus may be an ultrasound diagnostic device 1000. FIG. 1 is a block diagram of a configuration of the ultrasound diagnostic device 1000 according to an exemplary embodiment of the present invention. The ultrasound diagnostic device 1000 according to an exemplary embodiment of the present invention includes a probe 20, an ultrasound transmission/reception unit 100, an image processing unit 200, a communication unit 300, a memory 400, an input device 500, and a controller 600, and the components may be connected to one another via buses 700.

The ultrasound diagnostic device 1000 may be embodied not only as a cart type device but also as a portable type. Examples of portable ultrasound diagnostic devices may include a Picture Archiving and Communications System (PACS) viewer, a smartphone, a laptop computer, a personal digital assistant (PDA), and a tablet PC. However, exemplary embodiments are not limited thereto.

The probe 20 transmits ultrasound signals to an object 10, based on a driving signal applied by the ultrasound transmission/reception unit 100, and receives echo signals reflected from the object 10. The probe 20 includes a plurality of transducers that oscillate based on electric signals transmitted thereto and generate acoustic energy, that is, ultrasound waves. Furthermore, the probe 20 may be connected to a main body of the ultrasound diagnostic device 1000 by wires or wirelessly. According to embodiments of the present invention, the ultrasound diagnostic device 1000 may include a plurality of probes 20.

A transmission unit 110 supplies a driving signal to the probe 20 and includes a pulse generating unit 112, a transmission delaying unit 114, and a pulser 116. The pulse generating unit 112 generates pulses for forming transmission ultrasound waves based on a predetermined pulse repetition frequency (PRF), and the transmission delaying unit 114 applies a delay time for determining transmission directionality to the pulses. Pulses, to which a delay time is applied, correspond to a plurality of piezoelectric vibrators included in the probe 20, respectively. The pulser 116 applies a driving signal (or a driving pulse) to the probe 20 at a timing corresponding to each pulse to which a delay time is applied.

A reception unit 120 generates ultrasound data by processing echo signals received from the probe 20. The reception unit 120 may include an amplifier 122, an analog-to-digital converter (ADC) 124, a reception delaying unit 126, and a summing unit 128. The amplifier 122 amplifies echo signals in each channel, and the ADC 124 performs analog-to-digital conversion on the amplified echo signals. The reception delaying unit 126 applies delay times for determining reception directionality to the echo signals subjected to the analog-to-digital conversion, and the summing unit 128 generates ultrasound data by summing the echo signals processed by the reception delaying unit 126. According to exemplary embodiments, the reception unit 120 may not include the amplifier 122. In other words, if the sensitivity of the probe 20 or the capability of the ADC 124 to process bits is enhanced, the amplifier 122 may be omitted.

The image processing unit 200 generates an ultrasound image by scan-converting ultrasound data generated by the ultrasound transmission/reception unit 100 and displays the ultrasound image. In addition, an ultrasound image may include not only a gray-scale ultrasound image obtained by scanning an object in an amplitude (A) mode, a brightness (B) mode, and a motion (M) mode, but also a Doppler image representing a moving object by using a Doppler effect. The Doppler image may include a blood flow Doppler image (also called a color Doppler image) showing a flow of blood, a tissue Doppler image showing movement of tissue, and a spectral Doppler image showing a moving speed of an object as a waveform.

A B mode processing unit 212 extracts B mode components from ultrasound data and processes the B mode components. An image generating unit 220 may generate an ultrasound image indicating signal intensities as brightness based on the extracted B mode components.

Similarly, a Doppler processing unit 214 may extract Doppler components from ultrasound data, and the image generating unit 220 may generate a Doppler image indicating movement of an object as colors or waveforms based on the extracted Doppler components.

The image generating unit 220 according to an embodiment of the present invention may generate a 3D ultrasound image via volume-rendering of volume data and an elasticity image which shows the degree of deformation of the object 10 due to pressure. Furthermore, the image generating unit 220 may display additional information in an ultrasound image by using text and graphics. In addition, the generated ultrasound image may be stored in the memory 400.

A display unit 230 displays and outputs the generated ultrasound image. The display unit 230 may display and output not only an ultrasound image but also various information processed by the ultrasound diagnostic device 1000 on a screen via a graphical user interface (GUI). In addition, the ultrasound diagnostic device 1000 may include two or more display units 230 according to embodiments of the present invention.

The communication unit 300 is connected to a network 30 by wires or wirelessly and communicates with an external device or a server. The communication unit 300 may exchange data with a hospital server or another medical device in a hospital that is connected via a Picture Archiving and Communications System (PACS). Furthermore, the communication unit 300 may perform data communication according to the Digital Imaging and Communications in Medicine (DICOM) standard.

The communication unit 300 may transmit or receive data related to diagnosis of the object 10, e.g., an ultrasound image, ultrasound data, and Doppler data of the object 10, via the network 30. The communication unit 300 may also transmit or receive medical images obtained by other medical devices, such as a computed tomography (CT) image, a magnetic resonance (MR) image, and an X-ray image. Furthermore, the communication unit 300 may receive information related to a diagnosis history or a treatment schedule of a patient from a server and utilizes the information for diagnosing the patient. Furthermore, the communication unit 300 may perform data communication with a server or a medical device in a hospital as well as a portable terminal of a doctor or a patient.

The communication unit 300 is connected to the network 30 in a wired or wireless manner and may exchange data with a server 32, a medical device 34, or a portable terminal 36. The communication unit 300 may include at least one component that enables communication with external devices, e.g., a local area communication module 310, a wired communication module 320, and a mobile communication module 330.

The local area communication module 310 is a module for performing local area communication with a device within a predetermined distance. Examples of local area communication technology include a wireless Local Area Network (LAN), Wi-Fi, Bluetooth, ZigBee, Wi-Fi Direct (WFD), Ultra Wideband (UWB), Infrared Data Association (IrDA), Bluetooth Low Energy (BLE), and Near Field Communication (NFC), but are not limited thereto.

The wired communication module 320 is a module for performing communication by using an electric signal or an optical signal. Examples of wired communication technology include wired communication technologies using a pair cable, a coaxial cable, an optical fiber cable, and an Ethernet cable.

The mobile communication module 330 transmits or receives wireless signals to or from at least one of a base station, an external terminal, and a server on a mobile communication network. Here, the wireless signals may include voice call signals, video call signals, or various types of data for transmission and reception of text/multimedia messages.

The memory 400 stores various data processed by the ultrasound diagnostic device 1000. For example, the memory 400 may store not only medical data related to the diagnosis of the object 10, such as ultrasound data and ultrasound images that is input or output, but also algorithms or programs that are executed in the ultrasound diagnostic device 1000.

The memory 400 may be embodied as any of various storage media such as a flash memory, a hard disk drive, and Electrically Erasable Programmable Read-Only Memory (EEPROM). Furthermore, the ultrasound diagnostic device 1000 may utilize a web storage or a cloud server that functions as the memory 400 online.

The input device 500 is a means via which a user inputs data for controlling the ultrasound diagnostic device 1000. The input device 500 may include hardware components, such as a keypad, a mouse, a touch panel, a touch screen, a trackball, and a jog switch. However, exemplary embodiments are not limited thereto, and the input device 500 may further include various other input elements such as an electrocardiogram measuring module, a respiration measuring module, a voice recognition sensor, a gesture recognition sensor, a fingerprint recognition sensor, an iris recognition sensor, a depth sensor, a distance sensor, etc.

The controller 600 may control overall operations of the ultrasound diagnostic device 1000. In other words, the controller 600 may control operations among the probe 20, the ultrasound transmission/reception unit 100, the image processing unit 200, the communication unit 300, the memory 400, and the input device 500.

All or some of the probe 20, the ultrasound transmission/reception unit 100, the image processing unit 200, the communication unit 300, the memory 400, the input device 500, and the controller 600 may be operated by software modules. However, exemplary embodiments are not limited thereto, and some of the above components may be operated by hardware modules. Furthermore, at least one of the ultrasound transmission/reception unit 100, the image processing unit 200, and the communication unit 300 may be included in the controller 600, but are not limited thereto.

Figure 2:
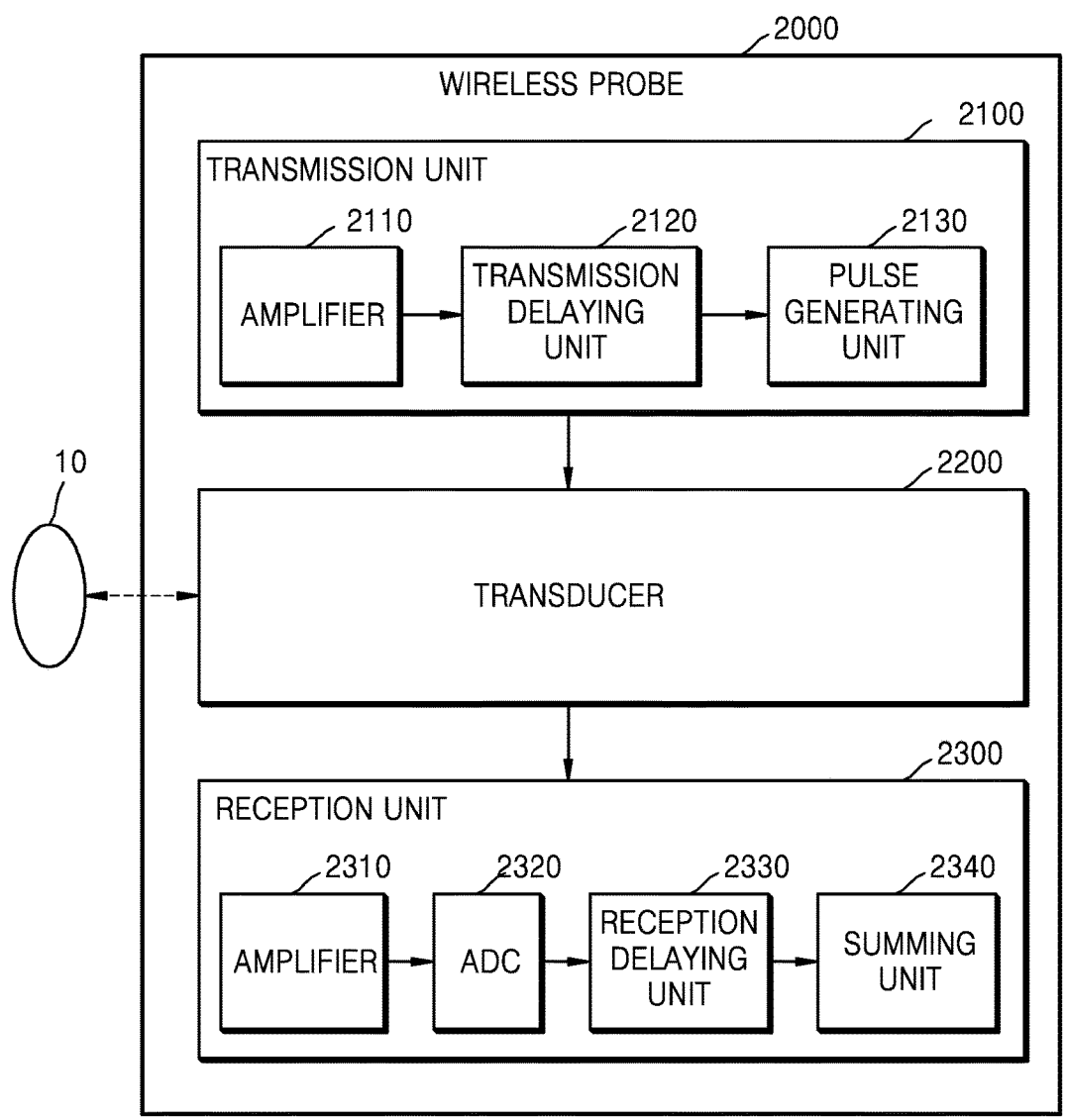
FIG. 2 is a block diagram of a configuration of a wireless probe related to an exemplary embodiment of the present invention.

FIG. 2 is a block diagram of a configuration of a wireless probe 2000 related to an exemplary embodiment of the present invention. As described above with reference to FIG. 1, the wireless probe 2000 includes a plurality of transducers. According to embodiments of the present invention, the wireless probe 2000 may include some or all of the components of the ultrasound transmission/reception unit 100.

The wireless probe 2000 of FIG. 2 includes a transmission unit 2100, a transducer 2200, and a reception unit 2300. Since each of the components is described above with reference to FIG. 1, detailed descriptions thereof are omitted herein. According to embodiments of the present invention, the wireless probe 2000 may selectively include a reception delaying unit 2330 and a summing unit 2340.

The wireless probe 2000 transmits ultrasound signals to an object 10, receives echo signals reflected from the object 10, generates ultrasound data, and wirelessly transmits the ultrasound data to the ultrasound diagnostic apparatus 1000 of FIG. 1.

Figure 3:
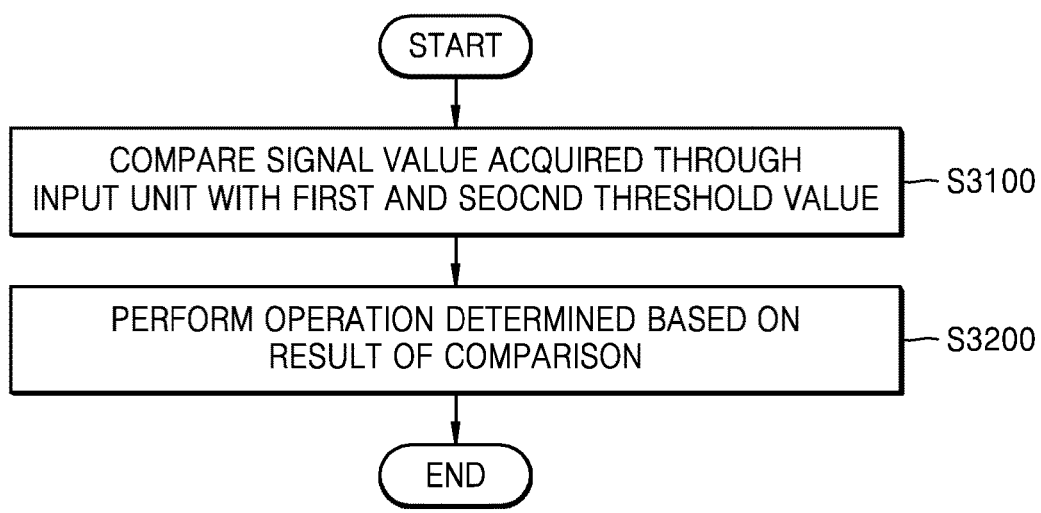
FIG. 3 is a flowchart of a process of controlling an ultrasound imaging apparatus according to an exemplary embodiment of the present invention.

FIG. 3 is a flowchart of a process of controlling an ultrasound imaging apparatus according to an exemplary embodiment of the present invention.

Referring to FIG. 3, first, the ultrasound imaging apparatus compares a signal value acquired through an input unit with a plurality of threshold values (S3100). In this case, the signal value may be a value of a signal that a user generates by using the input unit. For example, the signal value acquired through the input unit may be obtained by detecting the magnitude of pressure that is applied to the input unit that is capable of sensing the magnitude of pressure. As another example, the signal value may be obtained according to a position of the input unit that can be moved by the user. The input unit may be disposed on the input device (500 in FIG. 1) or located on one side of the probe (20 in FIG. 1). The input unit may be implemented in different ways according to embodiments of the present invention. For example, the input unit may include physical buttons, or soft buttons that are displayed on a touch screen.

In one embodiment, the ultrasound imaging apparatus may determine a state of the input unit based on the result of comparison between the signal value and the plurality of threshold values. For example, if first and second threshold values are 2 and 4, respectively, an ultrasound imaging apparatus may determine a state of the input unit as follows. The ultrasound imaging apparatus may determine that the input unit is in a first state if the signal value is less than or equal to 2, is in a second state if the signal value is greater than 2 and less than or equal to 4, and is in a third state if the signal value is greater than 4.

Subsequently, the ultrasound imaging apparatus may determine an operation to be performed by the ultrasound imaging apparatus itself, based on the result of comparison obtained in step S3100. In this case, the operation to be performed may be a process related to an ultrasound image. For example, the operation to be performed may be an operation of outputting a still image or storing an acquired ultrasound image. The ultrasound imaging apparatus may perform the determined operation by using at least of one of the image processing unit (200 in FIG. 1) and the controller (600 in FIG. 1) (S3200).

The ultrasound imaging apparatus may determine a state of the input unit according to the result obtained in operation S3100 and then an operation to be performed according to the determined state of the input unit. In one embodiment, the ultrasound imaging apparatus may determine an operation to be performed as the state of the input unit changes from one state to another. For example, if the input unit is in a first state, the ultrasound imaging apparatus may display an ultrasound image. When the input unit changes from the first state to a second state, the ultrasound imaging apparatus may display an ultrasound image, which is acquired at the time when the input unit transits to the second state, as a still image. Furthermore, if the input unit changes from the first state to a third state, the ultrasound imaging apparatus may store a displayed ultrasound image as a moving image. The ultrasound images may be acquired using a probe of the ultrasound imaging apparatus.

In one embodiment, if the input unit changes from the second state to the third state, the ultrasound imaging apparatus may store a still image displayed thereon. In addition, if the input unit changes from the third state to the first state while the ultrasound imaging apparatus is storing the ultrasound image as a moving image, the ultrasound imaging apparatus may terminate storage of the moving image.

Furthermore, the ultrasound imaging apparatus may determine an operation to be performed based on the length of time during which the state of the input unit remains the same. For example, if the input unit remains in the second state for more than 5 seconds, the ultrasound imaging apparatus may store a still image in a memory therein. Alternatively, the still image may be stored by using cloud computing instead of the memory. Exemplary embodiments are not limited thereto. The operation of the ultrasound imaging apparatus described above is presented by way of example only but not as a limitation. For example, the ultrasound imaging apparatus may output a normal elasticity image and a shear wave elasticity image if the input unit is in the first state and in the second state, respectively, and store an image in a memory if the input unit is in the third state.

Figure 4:
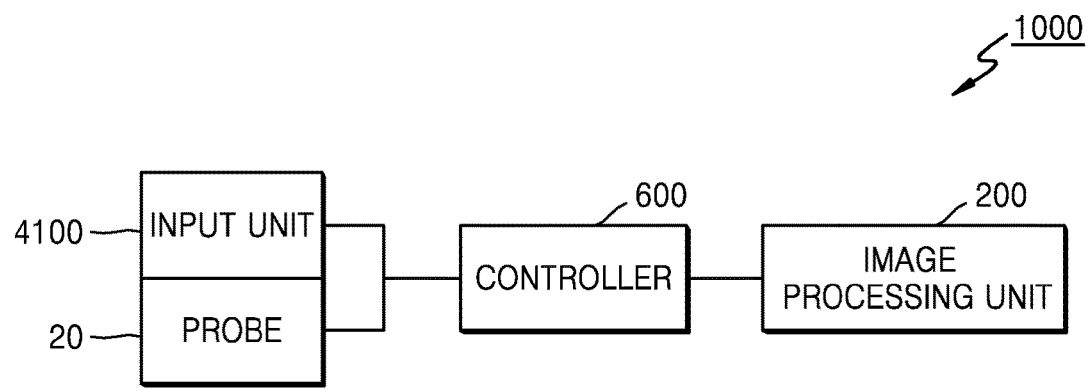
FIG. 4 is a block diagram of a configuration of an ultrasound imaging apparatus according to an exemplary embodiment of the present invention.

FIG. 4 is a block diagram of a configuration of an ultrasound imaging apparatus 1000 according to an exemplary embodiment of the present invention. The ultrasound imaging apparatus 1000 according to the present embodiment includes a probe 20, an input unit 4100, a controller 600, and an image processing unit 200. In this case, as described with reference to FIG. 1, the probe 20 transmits an ultrasound signal and receives an echo signal. The image processing unit 200 may acquire an ultrasound image based on a signal received through the probe 20.

The input unit 4100 may acquire a signal value. Here, the signal value is a value of a signal that a user generates by using the input unit 4100. For example, the signal value acquired through the input unit 4100 may be obtained by sensing the magnitude of pressure that is exerted on the input unit 4100 that is capable of sensing the magnitude of pressure. As another example, the signal value may be obtained according to a position of the input unit 4100 that can be moved by the user. The input unit 4100 may be disposed on the input device (500 in FIG. 1) or located on one side of the probe (20 in FIG. 1). The input unit 4100 may be implemented in different ways according to embodiments of the present invention. The input unit 4100 may include physical buttons, or soft buttons that are displayed on a touch screen.

In one embodiment, the controller 600 may determine a state of the input unit 4100 based on the result of comparison between the signal value and the plurality of threshold values. For example, if first and second threshold values are 2 and 4, respectively, the controller 600 may determine a state of the input unit 4100 as follows. The controller 600 may determine that the input unit 4100 is in a first state if the signal value is less than or equal to 2, is in a second state if the signal value is greater than 2 and less than or equal to 4, and is in a third state if the signal value is greater than 4.

The image processing unit 200 may determine an operation to be performed according to the state of the input unit 4100. The operation to be performed may be an image processing operation related to an ultrasound image. For example, the operation to be performed may be an operation of outputting a still image or storing an acquired ultrasound image. The image processing unit 200 may also display an ultrasound image obtained by image processing through a display unit (not shown).

In one embodiment, the image processing unit 200 may determine an operation to be performed as the state of the input unit 4100 changes from one state to another. For example, if the input unit 4100 is in the first state, the image processing unit 200 may display an ultrasound image through the display unit. When the input unit 4100 changes from the first state to a second state, the image processing unit 200 may display an ultrasound image, which is acquired at the time when the input unit 4100 transits to the second state, as a still image through the display unit. Furthermore, if the input unit 4100 changes from the first state to a third state, the image processing unit 200 may store a moving image generated from an ultrasound image displayed through the display unit. The ultrasound images may be acquired using the probe 20.

In one embodiment, if the input unit 4100 changes from the second state to the third state, the image processing unit 200 may store a still image displayed on the display unit. In addition, if the input unit 4100 changes from the third state to the first state while the ultrasound image is being stored as a moving image, the image processing unit 200 may terminate storage of the moving image.

Furthermore, the image processing unit 200 may determine an operation to be performed based on the length of time during which the state of the input unit 4100 remains the same. For example, if the input unit 4100 remains in the second state for more than 5 seconds, the image processing unit 200 may store a still image in a memory (not shown) included in the ultrasound imaging apparatus 1000. Alternatively, the still image may be stored by using cloud computing instead of the memory. However, embodiments of the present invention are not limited thereto.

Figure 5:
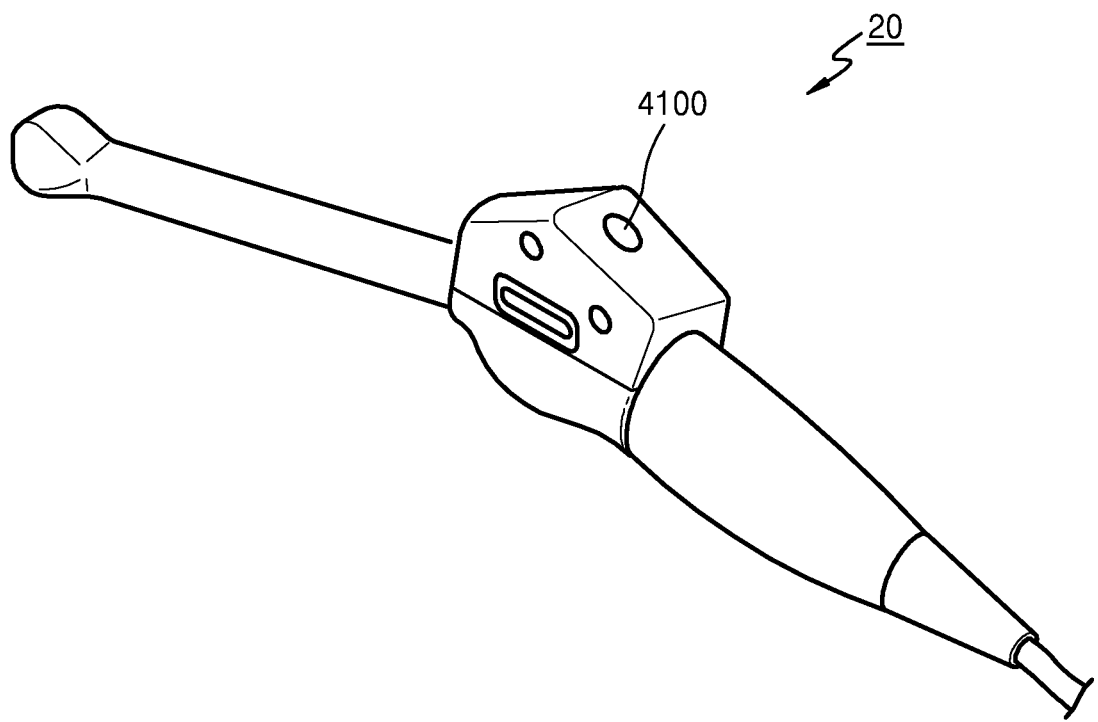
FIG. 5 illustrates a probe according to an exemplary embodiment of the present invention.

FIG. 5 illustrates a probe 20 according to an exemplary embodiment of the present invention. As shown in FIG. 5, an input unit 4100 may be disposed on one side of the probe 20. The structure shown in FIG. 5 is for the purpose of describing the present embodiment only, and embodiments of the present invention are not limited to the structure.

Figure 6:
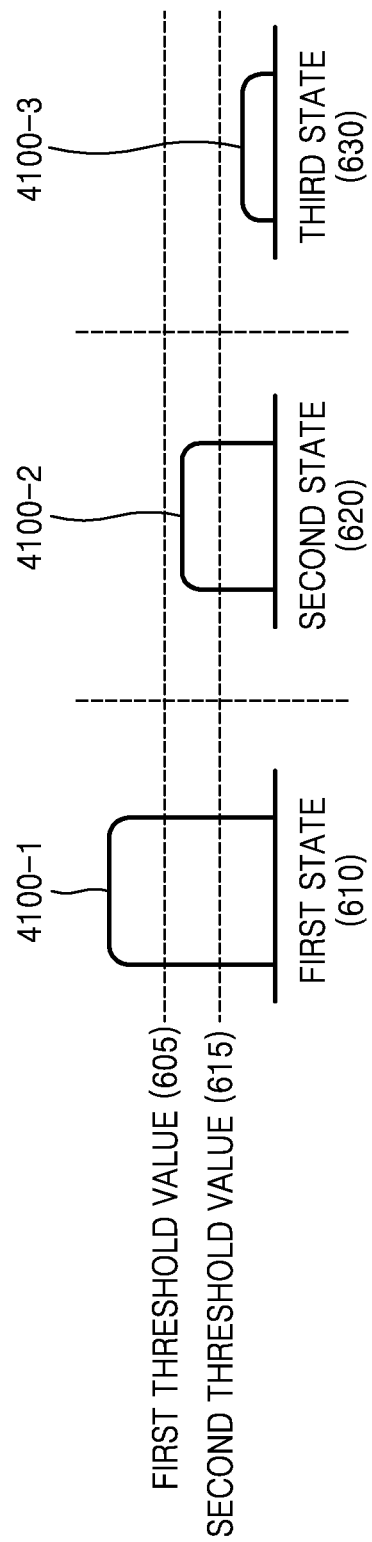
FIG. 6 illustrates an input unit according to an exemplary embodiment of the present invention.

FIG. 6 illustrates input units 4100-1, 4100-2, and 4100-3 according to an exemplary embodiment of the present invention.

If a pressure that is less than or equal to a first threshold value 605 is applied to the input unit 4100-1, an ultrasound imaging apparatus according to an embodiment of the present invention may determine the input unit 4100-1 as being in a first state 610. Furthermore, if a pressure that is greater than the first threshold value 605 and less than or equal to a second threshold value 615 is applied to the input unit 4100-2, the ultrasound imaging apparatus may determine the input unit 4100-2 as being in a second state 620. In addition, if a pressure greater than the second threshold value 615 is applied to the input unit 4100-3, the ultrasound imaging apparatus may determine the input unit 4100-3 as being in a third state 630.

The input units 4100-1, 4100-2, and 4100-3 may respectively detect positions thereof or pressures applied thereto and generate signal values corresponding to the positions or the pressures.

Referring to FIG. 6, the input unit 4100-1 cannot change from the first state directly to the third state 630 without passing through the second state 620. Thus, if the input unit 4100-1 changes from the first state 610 to the third state 630 through the second state 620 within a fixed time, the ultrasound imaging apparatus may determine that the input unit 4100-1 has changed from the first state 610 to the third state 630.

Figure 7:
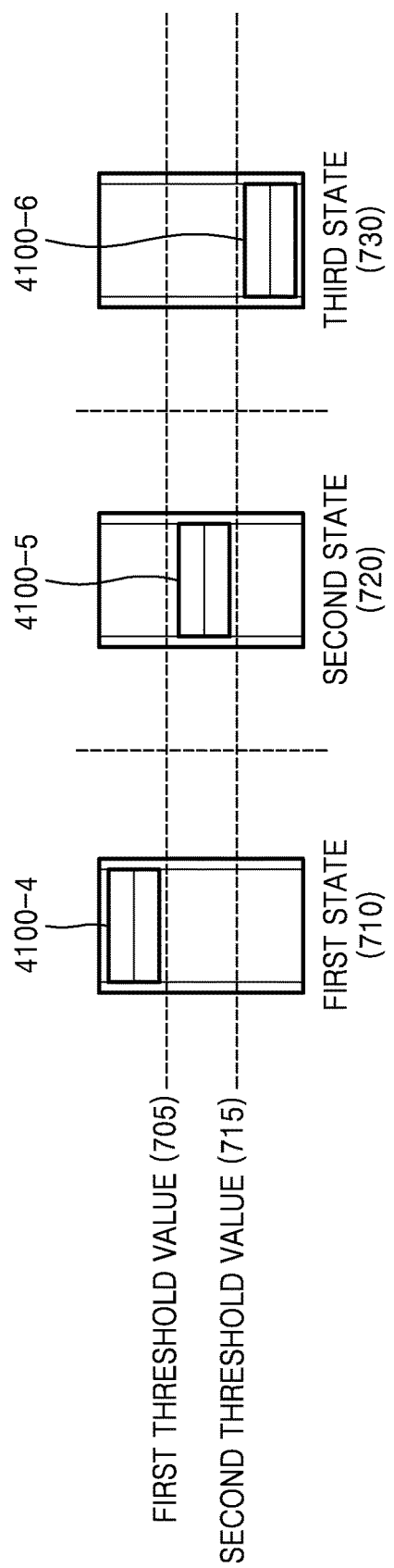
FIG. 7 illustrates an input unit according to another exemplary embodiment of the present invention.

FIG. 7 illustrates input units 4100-4, 4100-5, and 4100-6 according to another exemplary embodiment of the present invention.

As illustrated in FIG. 7, an ultrasound imaging apparatus may determine the input units 4100-4, 4100-5, and 4100-6 as being in one of a first state 710, a second state 720, and a third state 730, according to positions of the input units 4100-4, 4100-5, and 4100-6 that are classified by first and second threshold values 705 and 715.

Referring to FIG. 7, the input unit 4100-4 cannot change from the first state 710 directly to the third state 730 without passing through the second state 720. Thus, if the input unit 4100-4 changes from the first state 710 to the third state 730 through the second state 720 within a fixed time, the ultrasound imaging apparatus may determine that the input unit 4100-4 has changed from the first state 710 to the third state 730.

Although an input unit is classified into three (3) states based on two threshold values, the state of the input unit may be classified based on more than the two threshold values.

Exemplary embodiments of the present invention may be implemented through computer-readable recording media having recorded thereon computer-executable instructions such as program modules that are executed by a computer. Computer-readable recording media may be any available media that can be accessed by a computer and include both volatile and nonvolatile media and both detachable and non-detachable media. Furthermore, the computer-readable media may include computer storage media and communication media. The computer storage media include both volatile and nonvolatile and both detachable and non-detachable media implemented by any method or technique for storing information such as computer-readable instructions, data structures, program modules or other data. The communication media typically embody computer-readable instructions, data structures, program modules, other data of a modulated data signal, or other transmission mechanism, and they include any information transmission media.

While one or more embodiments of the present invention have been described with reference to the figures, it will be understood by those of ordinary skill in the art that various changes in form and details may be made therein without departing from the spirit and essential characteristics of the present invention as defined by the following claims. Thus, it should be understood that the exemplary embodiments described therein should be considered in a descriptive sense only and not for purposes of limitation. For example, components described as a single piece may be implemented in a distributed fashion, and similarly components described as being distributed may be implemented in a combined form.

Therefore, the scope of the invention is defined not by the embodiments but by the appended claims, and all modifications or variations within the scope of the appended claims and their equivalents will be construed as being included in the present invention.

What is claimed is:

1. A method of controlling an ultrasound imaging apparatus coupled to a probe, the method comprising steps of:
   (i) comparing, by the ultrasound imaging apparatus, a signal value acquired through an input unit disposed on one side of the probe with first and second threshold values;
   (ii) determining, by the ultrasound imaging apparatus, a state of the input unit as one of a first state, a second state, and a third state classified by the first threshold value and second threshold value, based on a result of the comparison;
   (iii) determining, by the ultrasound imaging apparatus, an ultrasound image processing operation corresponding to a change in the state of the input unit, wherein the change in the state of the input unit includes a change from one state of the first, second, and third states to another state of the first, second, and third states; and
   (iv) performing, by the ultrasound imaging apparatus, the determined ultrasound image processing operation,
   wherein the first threshold value is less than the second threshold value, and
   wherein the determining of the ultrasound image processing operation comprises:
      determining, by the ultrasound imaging apparatus, corresponding to determining the state of the input unit as the first state, the ultrasound image processing operation as acquiring an ultrasound image of an object by transmitting an ultrasound signal to the object by using the probe, and displaying the acquired ultrasound image,
      determining, by the ultrasound imaging apparatus, corresponding to determining the state of the input unit is changed from the first state to the third state, the ultrasound image processing operation as stopping transmission of the ultrasound signal to the object by using the probe, and displaying an ultrasound image being displayed before the state changes from the first state to the second state as a still image,
      determining, by the ultrasound imaging apparatus, corresponding to determining the state of the input unit is changed from the first state to the third state, the ultrasound image processing operation as storing an ultrasound image acquired through the probe as a moving image, and
      determining, by the ultrasound imaging apparatus, corresponding to determining the state of the input unit is changed from the second state to the third state, the ultrasound image processing operation as storing the displayed still image,
   wherein the ultrasound imaging apparatus includes:
      a probe configured to acquire the signal value and
      a controller configured to perform the steps (i) through (iv).

2. The method of claim 1, wherein the comparing of the signal value acquired through the input unit with the first and second threshold values comprises acquiring a signal that is determined according to the magnitude of a pressure applied to the input unit.

3. The method of claim 1, wherein the ultrasound image processing operation is further determined based on a length of time during which the input unit remains the same.

4. The method of claim 1, wherein the determining of the ultrasound image processing operation further comprises:
   upon determining that the state of the input unit is changed from the third state to the first state, controlling the ultrasound image processing operation to terminate the storing of the ultrasound image as the moving image.

5. The method of claim 1, wherein the determining of the ultrasound image processing operation further comprises:
   upon determining that the state of the input unit is changed from the third state to the second state, controlling the ultrasound image processing operation to display the still image.

6. The method of claim 1, wherein the comparing of the signal value acquired through the input unit with the first and second threshold values comprises acquiring a signal that is determined according to a position of the input unit.

7. A non-transitory computer-readable recording medium having recorded thereon a program for executing the method of claim 1 on a computer.

8. An ultrasound imaging apparatus comprising:
a probe having an input unit configured to acquire a signal value;
a controller including a memory communicatively connected to the controller, the controller configured to:
  determine a state of the input unit based on a result of comparing the signal value acquired through the input unit with first and second threshold values,
  determine a state of the input unit as one of a first state, a second state, and a third state classified by the first threshold value and second threshold value, based on a result of the comparison,
  determine an ultrasound image processing operation corresponding to a change in the state of the input unit,
wherein the change in the state of the input unit includes a change from one state of the first, second, and third states to another state of the first, second, and third states,
wherein the first threshold value is less than the second threshold value, and
wherein the controller is further configured to:
  determine the ultrasound image processing operation, corresponding to determining the state of the input unit as the first state, as acquiring an ultrasound image of an object by transmitting an ultrasound signal to the object by using the probe, and displaying the acquired ultrasound image,
  determine the ultrasound image processing operation, corresponding to determining the state of the input unit is changed from the first state to the second state, as stopping transmission of the ultrasound signal to the object by using the probe, and display an ultrasound image being displayed before the state changes from the first state to the second state,
  determine the ultrasound image processing operation, corresponding to determining the state of the input unit is changed from the first state to the third state, as storing an ultrasound image acquired through the probe as a moving image, and
  determine, corresponding to determining the state of the input unit is changed from the second state to the third state, the ultrasound image processing operation as storing the displayed still image.

9. The apparatus of claim 8, wherein the input unit acquires a signal that is determined according to the magnitude of a pressure applied to the input unit.

10. The apparatus of claim 8, wherein the controller is further configured to determine the ultrasound image processing operation based on a length of time during which the state of the input unit remains the same.

11. The apparatus of claim 8, wherein the controller is further configured to:
upon determining that the state of the input unit is changed from the third state to the first state, control the ultrasound image processing operation to terminate the storing of the ultrasound image as the moving image.

12. The apparatus of claim 8, wherein the controller is further configured to:
upon determining that the state of the input unit is changed from the third state to the second state, control the ultrasound image processing operation to display a still image.

13. The apparatus of claim 8, wherein the input unit acquires a signal that is determined according to a position of the input unit.

* * * * *